(12) United States Patent
Hosokawa et al.

(10) Patent No.: US 10,670,616 B2
(45) Date of Patent: Jun. 2, 2020

(54) MICROCHIP FOR ASSAY OF BLOOD PROPERTIES, AND DEVICE FOR ASSAY OF BLOOD PROPERTIES

(71) Applicant: FUJIMORI KOGYO CO., LTD., Tokyo (JP)

(72) Inventors: Kazuya Hosokawa, Tokyo (JP); Tomoko Wada, Tokyo (JP); Hisayo Kaneko, Tokyo (JP)

(73) Assignee: FUJIMORI KOGYO CO., LTD., Tokyo (JP)

( * ) Notice: Subject to any disclaimer, the term of this patent is extended or adjusted under 35 U.S.C. 154(b) by 0 days.

(21) Appl. No.: 15/302,337

(22) PCT Filed: Apr. 8, 2015

(86) PCT No.: PCT/JP2015/060993
§ 371 (c)(1),
(2) Date: Oct. 6, 2016

(87) PCT Pub. No.: WO2015/156322
PCT Pub. Date: Oct. 15, 2015

(65) Prior Publication Data
US 2017/0023596 A1   Jan. 26, 2017

(30) Foreign Application Priority Data

Apr. 8, 2014   (JP) .................. 2014-079693

(51) Int. Cl.
*G01N 33/49* (2006.01)
*G01N 33/86* (2006.01)
(Continued)

(52) U.S. Cl.
CPC ....... *G01N 33/86* (2013.01); *G01N 33/54306* (2013.01); *G01N 2333/7454* (2013.01); *G01N 2333/78* (2013.01)

(58) Field of Classification Search
CPC .............. G01N 33/4905; G01N 33/49; G01N 33/33487; G01N 33/48; G01N 33/86; G01N 33/50
(Continued)

(56) References Cited

U.S. PATENT DOCUMENTS

2005/0015001 A1*   1/2005   Lec .......................... A61B 8/12
                                                          600/369
2009/0311675 A1*  12/2009   Hosokawa ............. G01N 33/86
                                                              435/5

(Continued)

FOREIGN PATENT DOCUMENTS

JP   2001-221799   8/2001
JP   2013-200277   10/2013
(Continued)

OTHER PUBLICATIONS

Hosokawa et al, A novel automated microchip flow-chamber system to quantitatively evaluate thrombus formation and antithrombotic agents under blood flow conditions, Journal of Thrombosis and Haemostasis, 2011, 9: 2029-2037. (Year: 2011).*
(Continued)

*Primary Examiner* — Christine T Mui
(74) *Attorney, Agent, or Firm* — Foley & Lardner LLP

(57) ABSTRACT

A microchip for testing a blood property, comprising first and second channels for allowing a blood sample(s) to flow inside, wherein the first channel has a first reaction section coated with collagen and tissue thromboplastin; and said second channel has a second reaction section, wherein the second section has been coated with collagen and tissue thromboplastin the amount of which is equivalent to or smaller than the amount of tissue thromboplastin on said first channel, or the second section has been coated with collagen but not with tissue thromboplastin.

10 Claims, 6 Drawing Sheets

(51) Int. Cl.
*G01N 33/543* (2006.01)
*G01N 33/50* (2006.01)

(58) Field of Classification Search
USPC .............................. 422/73, 68.1, 50; 436/69
See application file for complete search history.

(56) References Cited

U.S. PATENT DOCUMENTS

| | | |
|---|---|---|
| 2010/0267066 A1 | 10/2010 | Hosokawa et al. |
| 2011/0039285 A1 | 2/2011 | Sadaba Champetier De Ribes et al. |
| 2011/0151500 A1 | 6/2011 | Hosokawa et al. |
| 2012/0301966 A1 | 11/2012 | Hosokawa et al. |
| 2012/0329082 A1* | 12/2012 | Viola .................... B01L 3/5027 435/13 |
| 2014/0038299 A1 | 2/2014 | Sadaba Champetier De Ribes et al. |

FOREIGN PATENT DOCUMENTS

| | | | |
|---|---|---|---|
| WO | WO 00/23802 * | 4/2000 | ............ G01N 33/49 |
| WO | WO-2006/065739 A2 | 6/2006 | |
| WO | WO-2006/066008 A2 | 6/2006 | |

OTHER PUBLICATIONS

Yamaguchi Y. et al., "Studies of a microchip flow-chamber system to characterize whole blood thrombogenicity in healthy individuals," Thromb Res., 2013.08, vol. 132, No. 2, p. 263-270.

Hosokawa K. et al., "A novel automated microchip flow-chamber system to quantitatively evaluate thrombus formation and antithrombotic agents under blood flow conditions," J Thromb Haemost., 2011.10, vol. 9, No. 10, p. 2029-2037.

Yamaguchi Y. et al., Thromb Res., 2013.08, vol. 132, No. 2, p. 263-270.

Hosokawa K. et al., J Thromb Haemost., 2011.10, vol. 9, No. 10, p. 2029-2037.

International Search Report for PCT Application Number PCT/JP2015/060993 dated Jun. 30, 2015.

International Preliminary Report on Patentability issued in related International Patent Application No. PCT/JP2015/060993, dated Oct. 20, 2016.

Bevers et al., Platelet Procoagulant Activity: Physiological Significance and Mechanisms of Exposure, Blood Reviews, 1991, pp. 146-154, vol. 5.

Extended European Search Report dated Sep. 13, 2017 issued in corresponding European application No. 15776057.0.

* cited by examiner (A)

(B)

(C)

MICROCHIP FOR ASSAY OF BLOOD PROPERTIES, AND DEVICE FOR ASSAY OF BLOOD PROPERTIES

RELATED APPLICATIONS

This application is the U.S. National Stage of International Patent Application Number PCT/JP2015/060993, filed Apr. 8, 2015, which claims priority to and the benefit of Japanese Patent Application Number 2014-079693, filed Apr. 8, 2014. The entire contents of the foregoing applications are hereby incorporated herein by reference for all purposes.

TECHNICAL FIELD

The present invention relates to a microchip to be used for investigating the thrombogenic capacity and the platelet function of blood at the same time using a small amount of the blood, and a test device using the same.

BACKGROUND ART

In thrombus formation or hemostatic reaction in the body, primary hemostasis, which occurs by platelet adhesion to collagen and aggregation reaction, and secondary hemostasis, which subsequently occurs by production of fibrin gel by activation of blood coagulation factors, proceed at the same time. Under arterial conditions, primary hemostasis, which mainly occurs by platelet aggregation reaction, is dominant, and, under venous conditions, secondary hemostasis, which occurs by blood coagulation reaction, is dominant over primary hemostasis, so that thrombi containing a larger amount of fibrin are formed.

The present inventors have developed thrombus monitoring devices and platelet function measuring devices using microchips (Patent Documents 1 to 4).

PRIOR ART DOCUMENTS

Patent Documents

Patent Document 1: WO 2007/046450
Patent Document 2: WO 2009/069656
Patent Document 3 WO 2010/018833
Patent Document 4: WO 2011/099569

SUMMARY OF THE INVENTION

Problems to be Solved by the Invention

In conventional blood tests, the platelet aggregability is measured for evaluating primary hemostasis, and the blood coagulation time is measured for evaluating secondary hemostasis. As described above, methods for analyzing the thrombogenic capacity and the platelet aggregability using a microchip have also been disclosed. However, there is no effective test method which enables simultaneous analysis of the primary hemostatic and secondary hemostatic capacities in a single assay for the purpose of analysis of factors involved in, and evaluation of therapeutic effects on, thrombosis and bleeding symptoms.

The present invention was made in view of the above circumstances, and aims to provide a device and a method that enable efficient simultaneous analysis of the primary hemostatic and secondary hemostatic capacities using a small amount of blood.

Means for Solving the Problems

In order to solve the problems described above, the present invention provides a microchip for testing a blood property, comprising first and second channels for allowing a blood sample(s) to flow inside, wherein the first channel has a first reaction section coated with collagen and tissue thromboplastin; and the second channel has a second reaction section wherein the second section has been coated with collagen and tissue thromboplastin the amount of which is equivalent to or smaller than the amount of tissue thromboplastin on said first channel, or the second section has been coated with collagen but not with tissue thromboplastin. Alternatively, since tissue thromboplastin is a component extracted from a tissue containing tissue factor, purified tissue factor having equivalent coagulation activity may be applied instead of tissue thromboplastin.

Preferably, the first reaction section is coated with a mixed solution of collagen, and tissue thromboplastin in an amount of not less than 1% by weight with respect to the collagen, and the second channel is coated with a mixed solution of collagen, and tissue thromboplastin whose weight ratio to the collagen is equivalent to or smaller than that in the first reaction section.

In the microchip for testing a blood property, each of the first reaction section and the second reaction section preferably has a channel dividing wall along the direction of blood flow.

In the microchip for testing a blood property, each of the first reaction section and the second reaction section preferably has a waste liquid storage section in its downstream side. This waste liquid storage section preferably has an absorbent material containing an anticoagulant.

The present invention also provides a device for testing a blood property, comprising: the microchip for testing a blood property; and a first blood storage container and a second blood storage container for introducing blood into the first channel and the second channel of the microchip for testing a blood property, respectively.

Here, the first blood storage container and the second blood storage container are preferably integrally molded.

The device for testing a blood property preferably comprises: a first pump connected to the first blood storage container, for allowing a blood sample to flow from the first blood storage container into the first channel, and a first pressure sensor for measuring the pressure applied to the first pump; and a second pump connected to the second blood storage container, for allowing a blood sample to flow from the second blood storage container into the second channel, and a second pressure sensor for measuring the pressure applied to the second pump.

The present invention also provides a method for measuring a blood property, the method comprising allowing a blood sample(s) to flow through the first and second channels using the device for testing a blood property, to analyze the thrombogenic capacity and the platelet function of the blood(s), for measuring the ratio between the primary hemostatic capacity and the secondary hemostatic capacity.

In a case where the first reaction section is coated with collagen and tissue thromboplastin, and allows formation of a thrombus composed of fibrin and platelets, and where the second reaction section is coated with only collagen, and allows formation of a platelet-specific thrombus, the difference between the compositions of the thrombi is obvious even if the flow rate is almost the same between the first channel and the second channel. Thus, by comparison of thrombus formation between the first reaction section and the second reaction section, evaluation and analysis of the primary hemostatic capacity and the secondary hemostatic capacity are possible. In such a case, the blood wall shear rate is preferably within the range of 1000 to 3000 s$^{-1}$ in both the first reaction section and the second reaction section.

On the other hand, in cases where both the first reaction section and the second reaction section are coated with collagen and tissue thromboplastin, mixed thrombi composed of platelets and fibrin are formed in both reaction sections. Thus, in cases where a higher wall shear rate (that is, a higher flow rate) than that in the first reaction section is used in the second reaction section, a thrombus containing a larger amount of platelets, which depends on the primary hemostatic capacity, is formed in the second reaction section, while a thrombus containing a larger amount of fibrin, wherein the blood coagulation reaction system is relatively dominant, is formed in the first reaction section. Since these thrombi have largely different compositions, the primary hemostatic and secondary hemostatic capacities can be evaluated by calculating the ratio between them.

Preferably, in such cases, the wall shear rates in those reaction sections are within the range of 300 s$^{-1}$ to 3000 s$^{-1}$; the wall shear rate in the first reaction section is less than 1200 s$^{-1}$; and the wall shear rate in the second reaction section is not less than 1200 s$^{-1}$. The wall shear rate in the second reaction section is preferably not less than 1.5 times, more preferably not less than 2 times, higher than the wall shear rate in the first reaction section.

The blood sample is preferably a blood sample treated with an inhibitor(s) of factor XII, and with an anticoagulant(s) selected from the group consisting of plasma kallikrein inhibitors, low-molecular-weight heparin, heparan sulfate, and synthetic pentasaccharides.

In the present invention, by coating the first channel and the second channel with equivalent amounts of collagen and tissue thromboplastin, adding a blood sample to the first channel, adding a sample prepared by adding a reagent (antiplatelet drug or hemostatic blood factor) such as a P2Y$_{12}$ inhibitor, PCC (prothrombin complex), or vWF (von Willebrand factor) to the blood sample to the second channel, and comparing the thrombogenic capacity between the first and second channels, causes of promotion or absence of the thrombogenic capacity in the blood sample can be analyzed.

Effect of the Invention

In the microchip for testing a blood property, and the device for testing a blood property using the microchip, according to the present invention, the first channel has the first reaction section coated with collagen and tissue thromboplastin; and the second channel has the second reaction section wherein the second section has been coated with collagen and tissue thromboplastin the amount of which is equivalent to or smaller than the amount of tissue thromboplastin on said first channel, or the second section has been coated with collagen but not with tissue thromboplastin. Thus, unlike the second channel, the first channel generates a thrombus containing more fibrin than platelet aggregates, wherein blood coagulation reaction is relatively dominant. On the other hand, since the second channel contains more platelets than the first channel does, thrombus formation based mainly on platelet aggregability occurs in the second channel. Thus, by analyzing the ratio between the thrombogenic capacities in these channels, comparative analysis of the balance between platelets and the coagulation system (that is, the balance between primary hemostasis and secondary hemostasis) is possible. In addition, inhibitory effects of various agents such as antiplatelet agents, anticoagulants, and hemostatic agents on primary hemostasis and secondary hemostasis can be analyzed.

In cases where the second reaction section does not contain tissue thromboplastin, and is coated only with collagen, a thrombus which is hardly influenced by the blood coagulation system, and is more specific to platelet aggregation, is formed.

This thrombus, which is specific to platelet aggregation, can be effectively suppressed by antiplatelet drugs such as aspirin and clopidogrel. On the other hand, aspirin and clopidogrel have less inhibitory effects on a thrombus containing fibrin and platelets as major components, which is formed in cases where collagen and tissue thromboplastin are used for the reaction section. Thus, by analyzing the ratio of thrombus formation between these reaction sections, the degree of effectiveness of an antiplatelet drug, or the degree of recovery of primary hemostasis by withdrawal of the effect of an antiplatelet agent during a washout period of the agent, can be quantitatively analyzed.

In cases where, in the microchip for testing a blood property, each of the first reaction section and the second reaction section has a waste liquid storage section in its downstream side, and this waste liquid storage section contains an absorbent material containing a solution of an anticoagulant such as citric acid, EDTA, or heparin, the labor of discharging the waste liquid to the outside of the microchip can be omitted, and adverse effects of the waste liquid on measurement results can be prevented.

In cases where the device for testing a blood property of the present invention comprises: a first pump connected to the first blood storage container, for allowing a blood sample to flow from the first blood storage container into the first channel, and a first pressure sensor for measuring the pressure applied to the first pump; and a second pump connected to the second blood storage container, for allowing a blood sample to flow from the second blood storage container into the second channel, and a second pressure sensor for measuring the pressure applied to the second pump; each of blood coagulation by fibrin, and platelet aggregation, can be quantitatively measured, which is preferred.

In cases where the first blood storage container and the second blood storage container are integrally molded, the measurement can be started by a single operation of an automatic pipette, which is preferred.

In the method for measuring a blood property using the device for testing a blood property of the present invention, the flow rate in the first channel is preferably less than 1200 s$^{-1}$, and the flow rate in the second channel is preferably not less than 1200 s$^{-1}$. The wall shear rate in the second reaction section is preferably not less than 1.5 times, more preferably not less than 2 times, higher than the wall shear rate in the first reaction section. By using a higher shear rate in the second channel than in the first channel as described above, the second channel can be allowed to generate a thrombus in which platelets are dominant relative to those in the first channel. Thus, the difference between the primary hemostatic capacity and the secondary hemostatic capacity of the blood sample can be evaluated more clearly by calculating the ratio between the thrombogenic capacities in those channels.

The blood sample is preferably a blood sample treated with a contact factor inhibitor, and with an anticoagulant selected from the group consisting of low-molecular-weight heparin, heparan sulfate, and synthetic pentasaccharides.

While low-molecular-weight heparin, heparan sulfate, and synthetic pentasaccharides effectively suppress clot formation in stationary blood, they have lower inhibitory effects on thrombus formation in the presence of blood flow. Thus, as a mixture with a contact factor inhibitor, they suppress blood coagulation in the blood storage container, but hardly inhibit thrombus formation and platelet aggregation in the channels of the microchip, so that more accurate measurement of thrombus formation in the reaction sections is possible, which is preferred. The contact factor inhibitor is preferably an inhibitor of blood coagulation factor XII.

In cases where a mixture of both a XII inhibitor and a plasma kallikrein inhibitor, and an anticoagulant selected from the group consisting of low-molecular-weight heparin, heparan sulfate, and synthetic pentasaccharides, is used, blood coagulation in the blood storage container is very strongly suppressed while thrombus formation in the microchip is hardly influenced, which is more preferred.

In terms of the blood collection tube, for example, an inhibitor of factor XII; an anticoagulant composed of a plasma kallikrein inhibitor, low-molecular-weight heparin, heparan sulfate, and a synthetic pentasaccharide; and calcium chloride; may be added to a blood collection tube containing sodium citrate, and the measurement may be carried out after canceling the anticoagulant capacity of citric acid. Alternatively, an inhibitor of factor XII and heparinase may be added to a blood collection tube containing heparin. In such a case, heparin is degraded into low-molecular-weight heparin by the heparinase, and its combination with the effect of the inhibitor of factor XII strongly suppresses coagulation in the reservoir.

In cases where the second channel does not contain tissue thromboplastin or tissue factor, and platelet-specific thrombus formation is to be analyzed, an antithrombin agent such as hirudin or argatroban may be used. In such cases, blood may be collected using a heparinized blood collection tube, and heparinase and the antithrombin agent may then be added thereto. This allows simple preparation of an antithrombin-treated blood sample for analysis in the second channel.

In the present invention, by using channels in which the first reaction section and the second reaction section are coated with equivalent amounts of collagen and tissue thromboplastin, adding a blood sample to the first channel, adding a sample prepared by supplementing the blood sample with, for example, a hemostatic blood factor such as a coagulation factor, or an antiplatelet drug, to the second channel; and comparing thrombus formation between the first and second reaction sections, causes of promotion or absence of the thrombogenic capacity in the blood sample can be analyzed.

For example, by adding a $P2Y_{12}$ inhibitor such as AR-C66096 to a blood sample from a patient taking clopidogrel, promotion of the thrombogenic capacity and the degree of $P2Y_{12}$ inhibition due to clopidogrel can be analyzed.

In cases where vWF or PCC is added to a blood sample with decreased hemostatic function, whether or not a decrease in the level of vWF or a coagulation factor is involved in the decrease in the hemostatic function can be analyzed. Further, such a test is useful for prediction of the therapeutic effect of administration of a vWF or PCC formulation in terms of whether or not the hemostatic function can be recovered by the administration.

For example, by analyzing a blood sample from a patient with VWD (von Willebrand disease) in the first channel, while analyzing a sample supplemented with vWF in the second channel, the therapeutic effect against VWD can be predicted.

EMBODIMENTS FOR CARRYING OUT THE INVENTION

First, the microchip for testing a blood property, and the device for testing a blood property, of the present invention are described with reference to drawings. However, the microchip for testing a blood property, and the device for testing a blood property, of the present invention are not limited to the following embodiments. In the present invention, "blood" includes whole blood and platelet-rich plasma. "Equivalent amount" means that the difference in the amount is within the range of, for example, ±10%.

Figure 1:
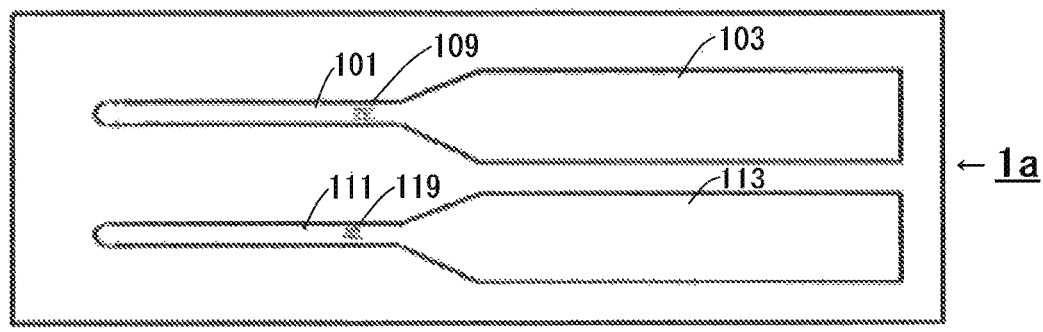
FIG. 1 is a diagram illustrating an embodiment of the microchip for testing a blood property of the present invention.
Figure 1:
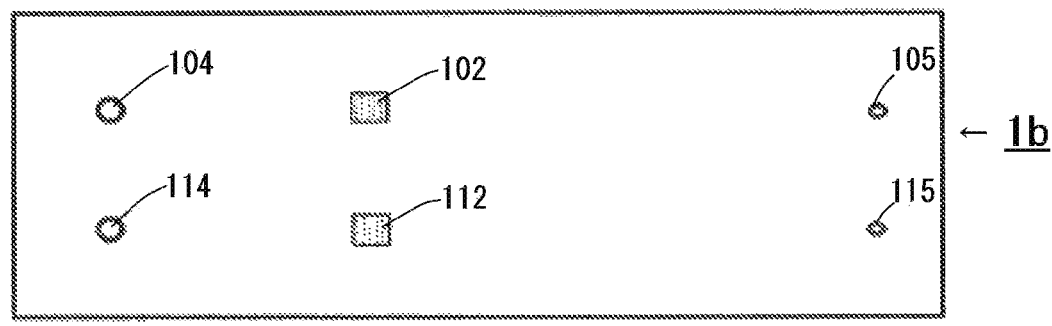
Figure 1:
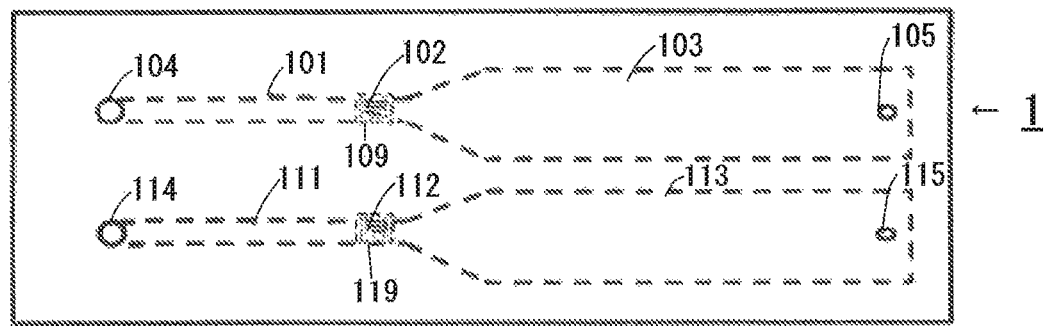

FIG. 1 is a schematic diagram illustrating the first embodiment of the microchip of the present invention. The following description is based on FIG. 1.

FIG. 1(A) is a plan view of a first substrate 1a of a microchip 1, wherein, on its surface, a first groove is formed to provide a first channel 101 and a first waste liquid storage section 103, and a second groove is formed to provide a second channel 111 and a second waste liquid storage section 113. The first groove and the second groove have shapes in which a first waste liquid storage section 103 is connected to the end opposite to the inlet-side end of the first channel 101, and a second waste liquid storage section 113 is connected to the end opposite to the inlet of the second channel 111.

In the first groove and the second groove, the later-mentioned channel dividing walls 109 and 119 are provided at positions overlapping with a first reaction section 102 and a second reaction section 112, respectively.

The cross-sectional shape of the groove corresponding to each channel is arbitrary, and examples of the shape include recessed shapes, U-shapes, and V-shapes. The depth of the groove corresponding to each channel is preferably 10 to 200 µm, and the width of the groove is preferably 10 µm to 3 mm.

The groove corresponding to each waste liquid storage section is preferably deeper than the groove corresponding to each channel, from the viewpoint of storage of a large amount of waste liquid. For example, the depth of the groove corresponding to each waste liquid storage section is 0.5 to 10 mm.

FIG. 1(B) is a plan view of a second substrate 1b of the microchip 1, wherein penetrating holes are formed to provide a first inlet 104 and a second inlet 114; and a first air hole 105 on the first waste liquid storage section, and a second air hole 115 on the second waste liquid storage section. The penetrating holes corresponding to the inlets 104 and 114 are formed such that their positions correspond to the inlet-side end of the first channel 101 and the inlet-side end of the second channel 111, respectively, on the first substrate 1a when the second substrate 1b is laminated with the first substrate 1a.

The penetrating holes corresponding to the air holes 105 and 115 are formed such that each of their positions corresponds to a part of the upper portion of the groove corresponding to the waste liquid storage section 103 or 113, respectively, on the first substrate 1a when the second substrate 1b is laminated with the first substrate 1a.

The second substrate 1b is coated with collagen, and tissue thromboplastin or tissue factor, at each of positions that partially overlap with the downstream sides of the first channel 101 and the second channel 111 when the second substrate 1b is laminated with the first substrate 1a, and these coated portions are provided as the first reaction section 102 and the second reaction section 112 when the second substrate 1b is laminated with the first substrate 1a.

The amount of the collagen coating is not limited as long as collagen is contained at a concentration which causes blood coagulation reaction. The amount of collagen coating is, for example, 1 to 100 µg/cm$^2$, especially preferably 10 µg/cm$^2$. The amount of collagen coating may be different between the first reaction section and the second reaction section, but these sections preferably have almost the same amount of collagen coating.

In terms of the collagen coating, as described in JP 05-260950 A and Blood. 1995 Apr. 1; 85(7): 1826-35, the coating can be simply carried out with high adhesive strength by, for example, a method in which collagen is dissolved in an acidic solution, and the resulting solution is applied to a predetermined position of a substrate made of glass, polystyrene, or the like, followed by washing and drying the substrate.

In cases where a hydrophobic resin or the like is to be coated, the coating can be carried out by subjecting the resin surface to hydrophilization treatment, applying a collagen solution to a desired area, and then subjecting the resin to natural drying or drying under reduced pressure.

In cases where a plastic is used as the base material, coating with collagen or collagen supplemented with tissue thromboplastin can be easily carried out by subjecting the surface of the plastic to hydrophilization treatment, applying a collagen solution to a desired area using a dispenser such as a pipette or a syringe, and then subjecting the plastic to natural drying or drying under reduced pressure.

In terms of the coating with tissue thromboplastin or tissue factor, stable immobilization by covalent bonding, besides bonding such as ionic bonding or hydrophobic bonding, is possible by, for example, introducing amino groups and/or carboxyl groups to the substrate and performing dehydration condensation using a water-soluble carbodiimide or the like. Alternatively, tissue thromboplastin may be mixed with collagen, followed by application and drying of the resulting mixture to perform coating with the tissue thromboplastin and coating with the collagen at the same time.

The amount of the tissue thromboplastin coating in the second reaction section is equivalent to or smaller than its amount in the first reaction section. Preferably, the amount of the tissue thromboplastin coating in the first reaction section is not less than 1.5 times larger than the amount in the second reaction section (that is, the amount in the second reaction section is not more than two thirds of the amount in the first reaction section). For example, the first reaction section is coated with tissue thromboplastin in an amount of not less than 1% by weight with respect to collagen, and the second reaction section is coated with tissue thromboplastin in an amount equivalent to or less than its amount in the first reaction section. In the second reaction section, the amount of the tissue thromboplastin coating may be 0.

FIG. 1(C) is a plan view of a microchip 1 obtained by laminating the first substrate 1a and the second substrate 1b with each other such that the surface of the first substrate on which the grooves are formed is in contact with the surface of the second substrate to which collagen and tissue thromboplastin are applied. The dash lines indicate that that the channels 101 and 111, reaction sections 102 and 112, and waste liquid storage sections 103 and 113 are present in the microchip 1.

Each of the first reaction section and the second reaction section may be provided with a plurality of channel dividing walls such as the ones disclosed in Patent Documents 3 and 4, which are present along the direction of blood flow and divide the width of each channel into a plurality of segments. By providing the dividing walls in the reaction section to which collagen and tissue thromboplastin are applied, clogging due to thrombus formation can be allowed to proceed faster in the dividing wall portion than in other portions. Since, as shown in FIG. 1, there is a sharp, two-dimensional or three-dimensional expansion (for a distance of not more than 10 mm) in the channel portion through which the blood passes after passing through the dividing walls, and this channel portion is connected to the waste liquid container, thrombus formation proceeds faster in the dividing wall portion compared to coagulation of the blood after passing through the dividing walls, thereby causing a pressure increase. Thus, a pressure analysis which specifically reflects thrombus formation in the dividing wall portion can be carried out.

The intervals between the channel dividing walls are preferably not more than 200 µm. In the channel dividing portion, the width of the channel is preferably separated into not less than five segments by the channel dividing walls. The shape of the channel dividing walls is not limited as long as the width of the channel can be separated into a plurality of segments. As described in Patent Document 4, the channel dividing walls may be treated such that surface roughness (Ra) is 10 to 200 nm.

A microchip having such channel dividing walls can be prepared by arranging a plurality of channel dividing walls at positions corresponding to the first reaction section and the second reaction section of the first substrate, and laminating the resulting first substrate with the second substrate.

In the waste liquid storage section, an absorbent material having a size which allows its placement in the waste liquid storage section may be arranged. Examples of the blood absorbent material include sponges and fabrics. The blood absorbent material may be impregnated with a solution of an anticoagulant(s) such as citric acid, EDTA, and/or heparin. By this, the waste liquid can be prevented from adversely affecting the measurement results due to its coagulation.

The material of the microchip is preferably a metal, glass, plastic, silicone, or the like. From the viewpoint of uses in blood monitoring (especially image analysis), the material is preferably transparent. From the viewpoint of formation of a circuit, the material is preferably a plastic, especially preferably a transparent plastic. In cases where the material is a silicone such as PDMS (polydimethylsiloxane), the substrates show excellent adhesiveness to each other, so that the first substrate and the second substrate can be laminated with each other by press bonding without adhesion using an adhesive or the like. However, in cases where a high pressure is applied to the inside of the microchip, an adhesive is preferably used. Poly(2-methoxyethyl acrylate) (PMEA) can be used for simply and effectively suppressing blood coagulation at unintended sites. The grooves and the holes to be provided on the substrates of the microchip can be formed using a cutter or laser beam. In cases where the material of the microchip is a plastic, they can be formed by injection molding. In cases of the formation by injection molding, microchips with uniform quality can be efficiently prepared, which is preferred.

The blood sample to be used in the method for measuring a blood property of the present invention is preferably an anticoagulated sample. Examples of the anticoagulation treatment agent to be used for the anticoagulation treatment include sodium or potassium citrate, sodium or potassium oxalate, ACD (Acid Citrate Dextrose), and ethylenediaminetetraacetic acid (EDTA) salts. Such anticoagulation treatment agents may be used as powders, freeze-dried products, or solutions such as aqueous solutions. Among these anticoagulation treatment agents, 3.2% sodium citrate, which is commonly used, is preferred since it is easily available. In such a case, it is preferred to use 1 volume of the anticoagulation treatment agent for 9 volumes of blood.

Other examples of the anticoagulation treatment agent include heparin, hirudin, thrombin aptamers, and a corn-derived trypsin inhibitor (1977. J. Biol. Chem 252. 8105). A plurality of anticoagulation treatment agents may be used.

More preferably, the anticoagulant is selected from the group consisting of plasma kallikrein inhibitors, low-molecular-weight heparin, heparan sulfate, and synthetic pentasaccharides. While plasma kallikrein inhibitors, low-molecular-weight heparin, heparan sulfate, and synthetic pentasaccharides efficiently suppress clot formation in stationary blood, they have lower inhibitory effects on thrombus formation in the presence of blood flow. Since they suppress blood coagulation in the blood storage container, but do not suppress thrombus formation and platelet aggregation in the channels of the microchip, more accurate measurement is possible, which is preferred. These anticoagulants are preferably used at low concentrations. Heparan sulfate is preferably used at a concentration of not more than 1 U/ml, and a pentasaccharide (for example, fondaparinux sodium) is preferably used at a concentration of not more than 2 µg/ml.

It is especially preferred to add an inhibitor of blood coagulation factor XII in addition to the anticoagulant selected from the group consisting of plasma kallikrein inhibitors, low-molecular-weight heparin, heparan sulfate, and synthetic pentasaccharides. Inhibitors of blood coagulation factor XII can more strongly suppress coagulation of stationary blood. By further addition of plasma, preferably a kallikrein inhibitor, thrombus formation in stationary blood can be even more strongly suppressed.

The anticoagulated blood can be obtained by, for example, a method in which the anticoagulation treatment agent is placed in a syringe or a vacuum blood collection tube in advance, followed by collection of blood, or a method in which the anticoagulation treatment agent is quickly added to blood immediately after collection.

The device for testing a blood property using a microchip 1 of the present invention is described below.

Figure 2:
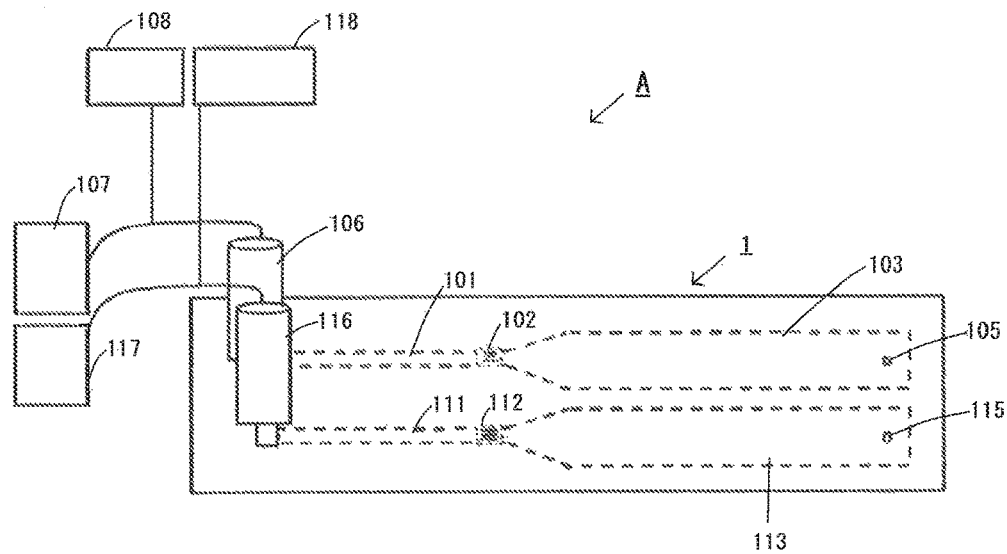
FIG. 2 is a diagram illustrating an embodiment of the device for testing a blood property of the present invention.

FIG. 2 is a schematic diagram illustrating a device for testing a blood property A as the first embodiment of the device for testing a blood property of the present invention, in which the microchip 1 is constituted by a transparent substrate and incorporated in the device. The first embodiment is described below based on FIG. 2.

To a first inlet 104 and a second inlet 114 of the microchip 1, reservoirs storing anticoagulated blood (blood storage containers) 106 and 116, respectively, are connected in inverted positions, and liquid transfer pumps 107 and 117 are connected to the reservoirs 106 and 116. To the liquid transfer pumps 107 and 117, pressure sensors 108 and 118 are connected. In cases where the reservoirs 106 and 116 are integrally molded, they can be easily handled, and simple measurement is possible.

As the liquid for the liquid transfer pumps 107 and 117, a liquid having a specific gravity lower than that of blood, such as mineral oil or physiological saline is used. This liquid is introduced using the liquid transfer pumps 107 and 117 into the reservoirs 106 and 116, respectively, in which blood is preliminarily filled, thereby overlaying the liquid on the blood. The liquid is then pushed using the pumps 107 and 117 to introduce the blood into the channels 101 and 111. By measuring the inflow pressure of the liquid, the inflow pressure of the blood into each channel can be indirectly measured.

More specifically, mineral oil is injected from the liquid transfer pumps 107 and 117 into the reservoirs 106 and 116. By this, the mineral oil is overlaid on the blood, and the blood is pushed into the channels 101 and 111 of the microchip 1. The blood passes through the channels 101 and 111, and then reaches the reaction sections 102 and 112. The blood, which is introduced from the inlets 104 and 114, passes through the channels 101 and 111, then passes through the reaction sections 102 and 112. Since, in this process, in the reaction section 102, the concentration of tissue thromboplastin is high, thrombus formation occurs mainly due to fibrin gel, and an increase in the inflow pressure due to this thrombus formation can be observed. On the other hand, in the reaction section 112, the concentration of tissue thromboplastin is low, so that platelet aggregation mainly occurs, resulting in an increase in the inflow pressure due to the platelet aggregation. By detecting the patterns of these pressure increases using the pressure sensors, and comparing the detected patterns, blood properties, that is, the thrombogenic capacity and the platelet aggregability, can be evaluated at the same time. The liquid transfer pumps are preferably capable of controlling the flow rate for the first channel and the flow rate for the second channel.

When thrombus formation that occurs mainly due to blood coagulation reaction is to be observed in the first channel, and thrombus formation that occurs mainly due to platelet aggregability is to be observed in the second channel, in cases where the first reaction section is coated with collagen and tissue thromboplastin, and the second reaction section is coated with only collagen, or the amount of tissue thromboplastin coating in the first reaction section is not less than 1.5 times larger than that in the second reaction section, the flow rate in the first reaction section and the flow rate in the second reaction section may be about the same. On the other hand, in cases where both the first reaction section and the second reaction section are coated with equivalent amounts of collagen and tissue thromboplastin, the wall shear rate in the first channel is preferably less than $1200 \text{ s}^{-1}$, and the wall shear rate in the second channel is preferably not less than $1200 \text{ s}^{-1}$; the wall shear rate in the second reaction section is more preferably not less than 1.5 times higher than that in the first reaction section. In such cases, thrombus formation due to fibrin gel is more likely to occur in the first channel, and platelet aggregation is more likely to occur in the second channel.

By using a microchip in which equivalent amounts of collagen and tissue thromboplastin are applied to the first reaction section and the second reaction section; allowing a blood sample to flow through the first channel; allowing a sample prepared by adding an antiplatelet drug or a hemostatic blood factor to the blood sample to flow through the second channel at the same flow rate; and comparing thrombus formation between the first and second channels; an effect of the drug, and a property of the blood sample in relation to the effect, can be analyzed. For example, when a sample derived from a patient with thrombosis is used as the blood sample, and an antiplatelet drug is added to the blood sample, in cases where the thrombus level is lowered, it can be effectively judged that the thrombosis is caused by promotion of platelet function, and that antiplatelet drugs are effective for the treatment. When vWF or PCC is added to a blood sample with decreased hemostatic function, whether or not a decrease in the level of vWF or a coagulation factor is involved in the decrease in the hemostatic function can be analyzed. Further, such a test is useful for prediction of the therapeutic effect of administration of a vWF or PCC formulation in terms of whether or not the hemostatic function can be recovered by the administration.

In such cases, the blood sample is preferably a blood sample subjected to anticoagulation treatment with a thrombin inhibitor such as hirudin or benzylsulfonyl-D-Arg-Pro-4-amidinobenzylamide (BAPA).

In cases where there are not less than three kinds of evaluation samples including a control (a sample to which an antiplatelet drug, hemostatic blood factor, or the like is not added), a plurality of microchips may be used. In such cases, the control blood sample may be allowed to flow through the first channel of any one of the microchips, and, in each of the other microchips, two kinds of evaluation samples (samples containing an antiplatelet drug or a hemostatic blood factor) may be allowed to flow through the first and second channels.

The blood subjected to the test reaches the waste liquid storage sections 103 and 113 from the ends of the channels 101 and 111, and is stored in these sections. In cases where a blood absorbent material such as a sponge impregnated with EDTA or the like is placed in each waste liquid storage section, the blood waste does not adversely affect the pressure measurement since it is absorbed into the blood absorbent material, and is not coagulated.

EXAMPLES

The present invention is described below in more detail by way of concrete Examples. However, the present invention is not limited to the Examples.

[Preparation of Microchip, and Device for Testing Blood Property]

Two transparent substrates, that is, the first substrate 1a shown in FIG. 1(A) and the second substrate 1b shown in FIG. 1(B) (injection-molded products manufactured by Richell Corporation), were prepared. In the first substrate 1a, each of the channels 101 and 111 has a length of 20 mm, depth of 40 μm, and width of 2 mm, and each of the waste liquid storage sections has a length of 30 mm, depth of 1.3 mm, and width of 8.5 mm.

In the substrate 1a, 25 dividing walls each having a height of 40 μm, width of 40 μm, and length of 1.5 mm were arranged at equal intervals at positions corresponding to the first reaction section and the second reaction section of the first channel and the second channel, to provide channel dividing walls 109 and 119, respectively.

In the second substrate 1b, the holes corresponding to the inlets 104 and 114 were provided as penetrating holes each having an inner diameter of 2 mm and a circular cross-sectional shape. On the other hand, the holes corresponding to the air holes 105 and 115 were provided as penetrating holes each having an inner diameter of 1 mm and a circular cross-sectional shape. A position that corresponds, when the second substrate 1b is laminated with the first substrate, to a part of the downstream side of the channel 101 was coated with collagen and tissue thromboplastin. On the other hand, a position that corresponds, when the second substrate 1b is laminated with the first substrate, to a part of the downstream side of the channel 111 was coated with only collagen. The concentrations of the collagen and the tissue thromboplastin used for the coating, and the coating method, were as follows.

In the substrate 1b, a solution prepared by mixing 3 mg/ml collagen solution and 0.4 mg/ml tissue thromboplastin solution at a ratio of 1:1 was applied to the position corresponding to the first reaction section 102, and only 0.75 mg/ml collagen solution was applied to the position corresponding to the second reaction section 112, such that each applied area has a size of 6 mm×6 mm.

Example 1

The first substrate 1a and the second substrate 1b were laminated with each other by using a silane coupling agent and heat pressing at 60° C. for 3 hours, such that the surface of the first substrate 1a on which the grooves open and the surface of the second substrate 1b to which collagen and tissue thromboplastin were applied face inward, to provide the microchip 1 shown in FIG. 1(C).

The microchip 1 prepared was placed on a stage which is not shown in the figure, and, as shown in FIG. 2, reservoirs 106 and 116 were connected to inlets 104 and 114 of the microchip 1. Pumps 107 and 117 were connected to the reservoirs 106 and 116 through tubes, and the pressures applied to the pumps were measured using pressure sensors 108 and 118.

An experiment was carried out with blood collected from a healthy individual using a 3.2% sodium citrate blood collection tube (Terumo Corporation) and a hirudin blood collection tube (final concentration, 25 μg/ml; Roche diagnostics K.K.).

Figure 3:
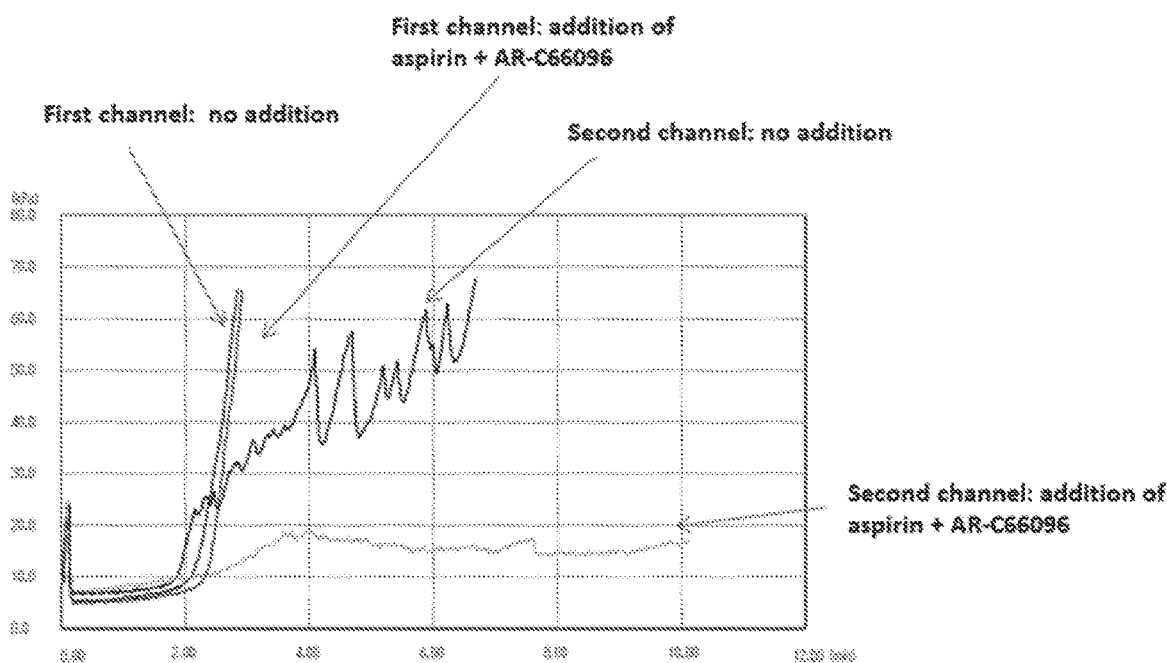
FIG. 3 is a diagram showing the pressure waveforms in Example 1 and Example 2-1.

Blood prepared by adding 12 mM (final concentration) calcium chloride and 50 μg/ml corn trypsin inhibitor (CTI) to the citrate blood was added to the first channel, and the hirudin-treated blood was added to the second channel. Using the analysis device shown in FIG. 2, the first channel and the second channel were perfused with the bloods at a flow rate of 18 μl/min. for 10 minutes while pressure analysis was carried out. The pressure waveforms were as shown in FIG. 3. The integrated values of the areas below 60 kPa were 457 and 372, respectively.

Example 2-1

The same measurement as in Example 1 was carried out except that 10 mM aspirin and 100 μM P2Y$_{12}$ inhibitor AR-C66096 (Tocris Bioscience) were added to each of the citrate blood and the hirudin blood. The pressure waveforms were as shown in FIG. 3. The integrated values of the areas below 60 kPa were 450 and 65, respectively.

Example 2-2

The same measurement as in Example 1 was carried out except that 3 μg/ml abciximab or 200 nM OS-1 (GPIb-inhibitory peptide) was added to each of the citrate blood and the hirudin blood. The integrated values of the areas below 60 kPa were 27.0 and 47.9, respectively, in the first channel, and 5.4 and 15.0, respectively, in the second channel.

According to Examples 1 and 2, it can be seen that thrombus formation was remarkably suppressed in the second channel as compared to the first channel, by the actions of aspirin and the P2Y$_{12}$ inhibitor. The ratio between the integrated values for the first channel and the second channel was 0.81 before the addition of the agents, and 0.14 after the addition of the agents. On the other hand, in the cases where the GPIIb/IIIa inhibitor abciximab or the GPIb inhibitor OS-1 was added, thrombus formation was suppressed in both the first channel and the second channel. Thus, comparison of the effects of the antiplatelet drugs was possible.

Example 3

An experiment was carried out with blood collected from a healthy individual using a heparin blood collection tube (3 ml) manufactured by Beckton Dickinson.

To the collected blood, 0.1 U/ml heparinase and, as a XII factor inhibitor, 50 μg/ml (final concentration) CTI were added, and the reaction was then allowed to proceed at room temperature for 10 minutes. The resulting blood was added to the first channel. To the collected blood, 0.1 U heparinase and 25 μg/ml (final concentration) hirudin were added, and the reaction was then allowed to proceed at room temperature for 10 minutes. The resulting blood was added to the second channel. Using the analysis device shown in FIG. 2, the channels were perfused with the bloods at a flow rate of 24 μl/min. (initial wall shear rate, about 2000 s$^{-1}$) for 10 minutes while pressure analysis was carried out.

Figure 4:
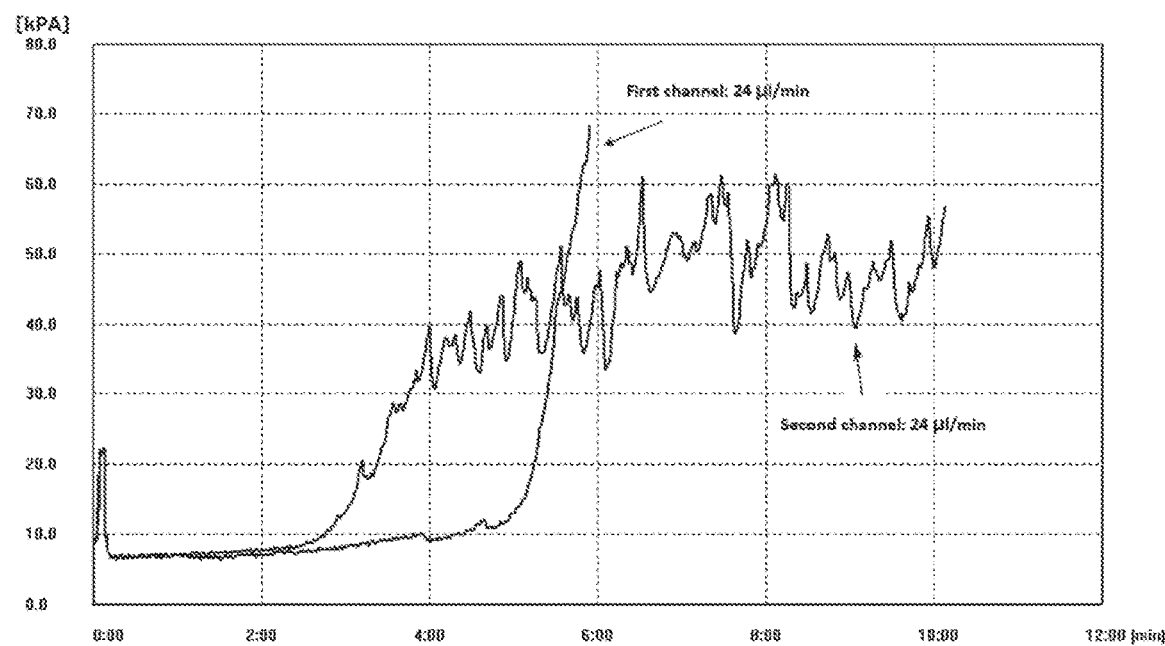
FIG. 4 is a diagram showing the pressure waveforms in Example 3.

The pressure waveforms were as shown in FIG. 4. The integrated values of the areas below 60 kPa were 285 and 258, respectively.

By the addition of heparinase, and the FXII inhibitor or hirudin to the heparin blood, thrombus formation in the second channel could be analyzed.

Example 4-1

A microchip having the same shape as in Examples 1 to 3 was prepared, and, in the second substrate 1b, a solution prepared by mixing 3 mg/ml collagen solution and 0.4 mg/ml tissue thromboplastin solution at a ratio of 1:1 was applied to the positions corresponding to the first reaction section 102 and the second reaction section 112 such that each applied area has a size of 6 mm×6 mm. The microchip prepared was used in the following experiment.

Blood was collected using a blood collection tube containing 3.2% sodium citrate, manufactured by Terumo Corporation. To the collected blood, 50 μg/ml (final concentration) CTI and 12 mM (final concentration) calcium chloride were added, and the resulting blood was used for perfusion of the first channel at a flow rate of 8 μl/min. (initial wall shear rate, about 660 s$^{-1}$) and the second channel at a flow rate of 24 μl/min. (initial wall shear rate, about 2000 s$^{-1}$) for 10 minutes while pressure analysis was carried out.

Example 4-2

The same experiment as in Example 4-1 was carried out using (1) blood prepared by 2-fold dilution of the citrate blood with physiological saline; (2) blood prepared by adding a 0.5 U vWF (von Willebrand factor) formulation (CSL-Behring) to the 2-fold diluted blood of (1); (3) blood prepared by adding a 0.5 U PCC formulation (CSL-Behring) to the 2-fold diluted blood of (1); (4) blood prepared by adding 1 U heparin; or (5) blood prepared by adding 3 μg/ml Abciximab (Eli Lilly).

The integrated values of the pressures measured for 10 minutes, and the ratios between the first channel and the second channel are shown in the following Table 1.

TABLE 1

|  | 8 μL/min first channel | 24 μL/min second channel |
| --- | --- | --- |
| Control | 409.3 | 482 |
| 50% dilution | 203.9 | 248.2 |
| 50% dilution + 0.5 U/ml vWF | 171.2 | 381.1 |
| 50% dilution + 0.5 U/ml PCC | 324.5 | 270.4 |
| Heparin 1 U/ml | 127.3 | 328.4 |
| abciximab 3 μg/ml | 394.8 | 20.5 |

From these results, it was found that anticoagulants strongly suppress thrombi in the first channel, while antiplatelet drugs more strongly suppress thrombi in the second channel. After the blood dilution, the addition of the coagulation factor (PCC) led to remarkable recovery of thrombi in the first channel, and the addition of vWF led to remarkable recovery of thrombi in the second channel.

Comparative Example 1

Figure 5:
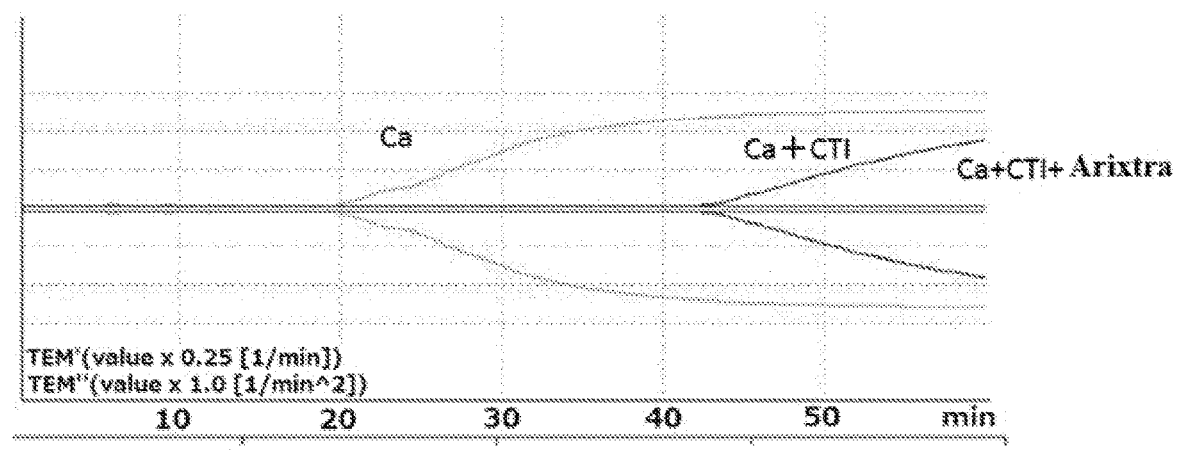
FIG. 5 is a diagram showing the analysis results in Comparative Example 1.

Blood was collected using a blood collection tube containing 3.2% sodium citrate, manufactured by Terumo Corporation. To the collected blood, 12 mM calcium chloride; 12 mM calcium chloride and 50 μg/ml CTI; or 12 mM calcium chloride, 50 μg/ml CTI, and 1 μg/ml Arixtra (synthetic pentasaccharide, GlaxoSmithKline K.K.); was/were added, and each resulting blood was analyzed by ROTEM (Tem International GmbH). The results are shown in FIG. 5.

It was shown that addition of CTI and a synthetic saccharide strongly suppresses blood coagulation in the absence of blood flow.

On the other hand, in the case of Example 4-1, no remarkable change in the pressure waveform was found even by further addition of Arixtra at a high concentration (0.5 μg/ml) to the blood.

Example 5

Canine blood was anticoagulated with 3.2% sodium citrate. Subsequently, 50 µg/ml (final concentration) CTI and 12 mM (final concentration) calcium chloride were added to the blood, and the resulting blood was used for perfusion of the first channel at a flow rate of 24 µl/min. and the second channel at a flow rate of 8 µl/min. for 10 minutes while pressure analysis was carried out.

Example 6

An experiment was carried out in the same manner as in Example 5 except that 0.5 U danaparoid sodium was added to the dog sodium citrate blood.

Comparative Example 2

Canine blood was anticoagulated with 3.2% sodium citrate. Subsequently, 12 mM calcium chloride; 50 µg/ml (final concentration) CTI and 12 mM (final concentration) calcium chloride; or 0.5 U/ml (final concentration) danaparoid sodium, 50 µg/ml CTI, and 12 mM (final concentration) calcium chloride; was/were added to the blood, and blood coagulation in the absence of blood flow was analyzed by ROTEM (Tem International GmbH).

Figure 6:
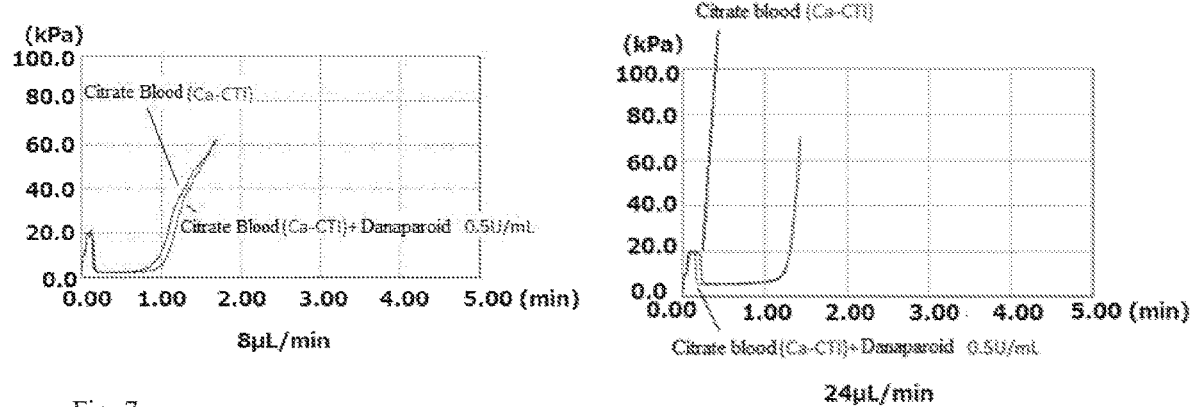
FIG. 6 is a diagram showing the pressure waveforms in Examples 5 and 6.
Figure 7:
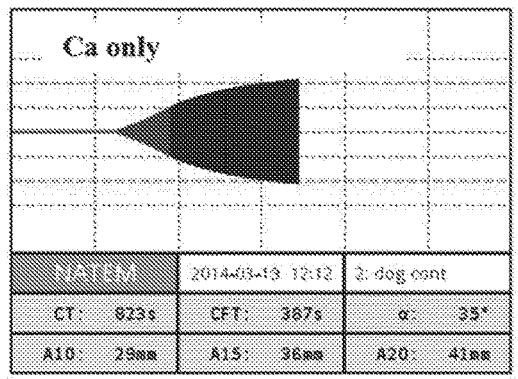
FIG. 7 is a diagram showing the analysis results in Comparative Example 2.
Figure 7:
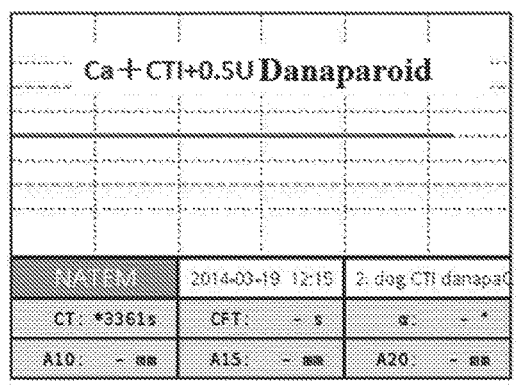
Figure 7:
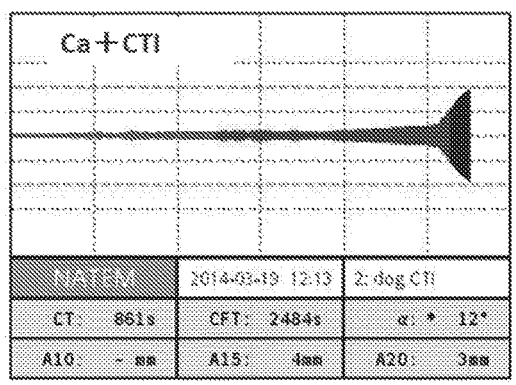

The pressure waveforms of Examples 5 and 6 are shown in FIG. 6. Analysis results in Comparative Example 2 are shown in FIG. 7.

Comparative Example 2 demonstrated that addition of danaparoid sodium (0.5 U/ml) leads to remarkable delay of blood coagulation in the absence of blood flow, while Examples 5 and 6 demonstrated that its addition hardly suppresses white thrombi in the presence of blood flow.

Example 7-1

The same microchip as in Examples 1 to 3 was used except that, in the second substrate 1b, a solution prepared by mixing 3 mg/ml collagen solution and 0.4 mg/ml tissue thromboplastin solution at a ratio of 1:1 was applied to the positions corresponding to the first reaction section 102 and the second reaction section 112 such that each applied area has a size of 6 mm×6 mm. The microchip prepared was used in the following experiment.

Blood was collected using a blood collection tube containing 3.2% sodium citrate, manufactured by Terumo Corporation. The first channel was perfused with blood prepared by adding 50 µg/ml (final concentration) CTI and 12 mM (final concentration) calcium chloride to the collected blood, and the second channel was perfused with blood prepared by 2-fold dilution of the citrate blood with Lactec Injection (Otsuka Pharmaceutical Co., Ltd.) and subsequent addition of 50 µg/ml CTI and 12 mM (final concentration) calcium chloride thereto. The perfusion of the channels was carried out at a flow rate of 24 µl/min. for 10 minutes while the pressures in the channels were continuously analyzed.

Example 7-2

Subsequently, the same measurement as in 7-1 was carried out under the same conditions as described above except that blood prepared by 2-fold dilution with Lactec Injection and subsequent addition of 0.5 U/ml (final concentration) PCC was added to the first channel, and that blood prepared by 2-fold dilution with Lactec Injection and subsequent addition of 0.5 U/ml (final concentration) vWF was added to the second channel.

Example 7-3

Subsequently, the same measurement as in 7-1 was carried out under the same conditions as described above except that blood prepared by 2-fold dilution with Lactec Injection and subsequent addition of 0.25 U/ml (final concentration) heparin was added to the first channel, and that blood prepared by 2-fold dilution with Lactec Injection and subsequent addition of 2 µg/ml (final concentration) abciximab was added to the second channel.

Figure 8:
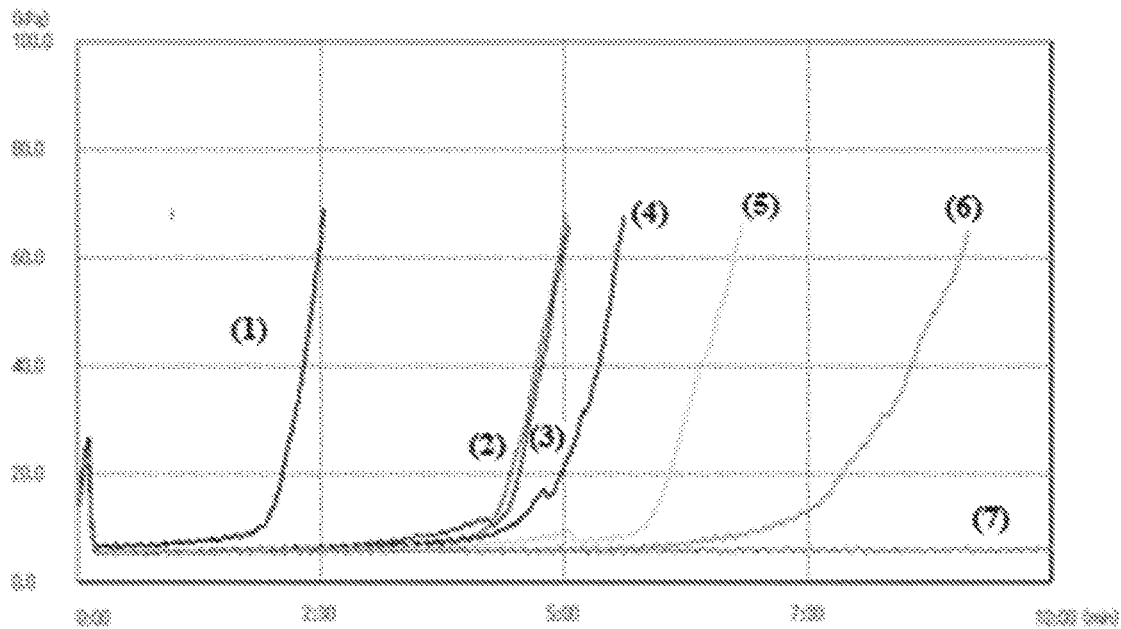
FIG. 8 is a diagram showing the pressure waveforms in Example 7. (1) Control; (2) 2-fold dilution with Lactec+addition of 0.5 U/ml vWF; (3) 2-fold dilution with Lactec+addition of 0.5 U/ml PCC; (4) 2-fold dilution with Lactec; (5) 2-fold dilution with Lactec+addition of 1 μg/ml abciximab; (6) 2-fold dilution with Lactec+addition of 0.25 U/ml heparin; (7) 2-fold dilution with Lactec+addition of 0.5 U/ml heparin.

The resulting pressure waveforms are shown in FIG. 8.

Examples 8-1 to 8-3

Measurement was carried out in the same manner as in Examples 7-1, 7-2, and 7-3 except that the flow rate was 8 µl/min.

Figure 9:
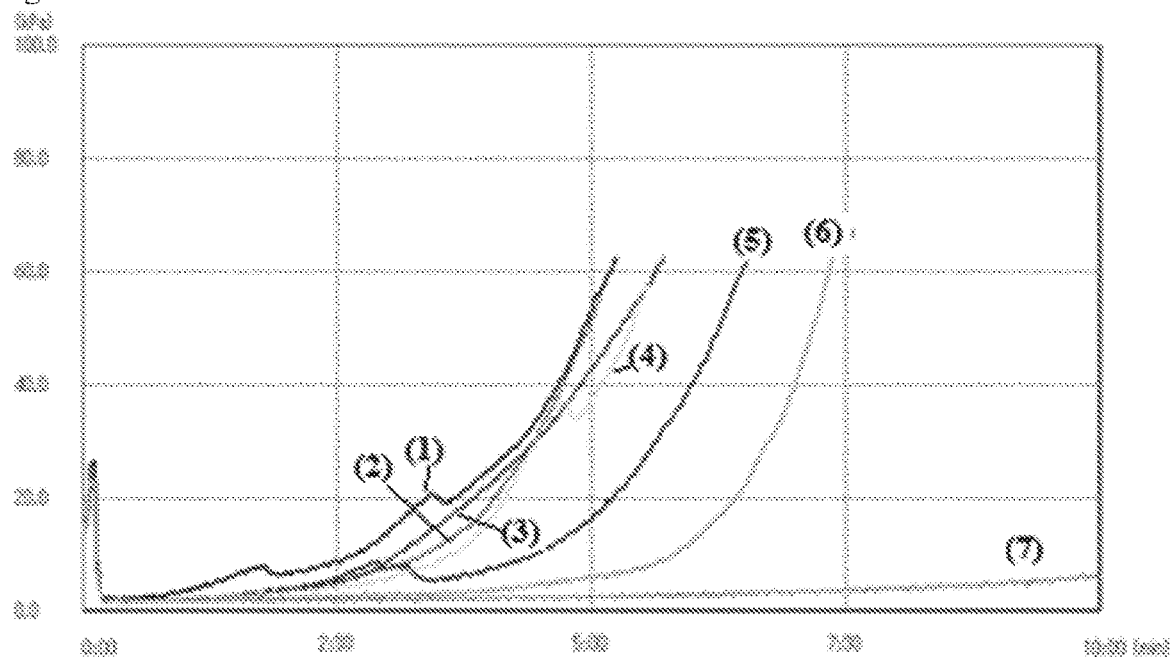
FIG. 9 is a diagram showing the pressure waveforms in Example 8. (1) Control; (2) 2-fold dilution with Lactec+addition of 0.5 U/ml vWF; (3) 2-fold dilution with Lactec+addition of 0.5 U/ml PCC; (4) 2-fold dilution with Lactec+addition of 1 μg/ml Abciximab; (5) 2-fold dilution with Lactec; (6) 2-fold dilution with Lactec+addition of 0.25 U/ml heparin; (7) 2-fold dilution with Lactec+addition of 0.5 U/ml heparin.

The pressure waveform patterns were as shown in FIG. 9.

Examples 7 and 8 demonstrate that, by performing the measurement for the first channel and the second channel under the same conditions to analyze changes after addition of reagents such as vWF and PCC, a decrease in hemostatic function due to, especially, dilution of blood, and the recovering effects of vWF, PCC agents, and the like, can be analyzed.

Thus, the above analysis is useful for predicting which agent, by its administration, allows recovery of hemostatic function especially after dilution of blood.

Example 9

The same microchip as in Examples 1 to 3 was used, except that, in the second substrate 1b, a solution prepared by mixing 3 mg/ml collagen and 0.4 mg/ml tissue thromboplastin solution at a ratio of 1:1 and a solution prepared by mixing 3 mg/ml collagen and 0.2 mg/ml tissue thromboplastin solution at a ratio of 1:1 were applied to the positions corresponding to the first reaction section 102 and the second reaction section 112, respectively, such that each applied area has a size of 6 mm×6 mm. The microchip prepared was used in the following experiment.

Blood was collected using a blood collection tube containing 3.2% sodium citrate, manufactured by Terumo Corporation. To the collected blood, 50 µg/ml (final concentration) CTI and 12 mM (final concentration) calcium chloride were added, and the resulting blood was used for perfusion of the first channel at a flow rate of 8 µl/min. and the second channel at a flow rate of 24 µl/min. for 10 minutes while pressure analysis was carried out.

Example 10

The same experiment as in Example 9 was carried out except that blood prepared by 2-fold dilution with physiological saline (Otsuka Pharmaceutical Co., Ltd.), blood prepared by 2-fold dilution with physiological saline+addition of 0.5 U/ml vWF (CSL-Behring), blood prepared by 2-fold dilution+addition of 0.5 U/ml PCC (CSL-Behring), blood prepared by addition of 1 U/ml heparin, or blood prepared by addition of 2 µg/ml abciximab, was used. The areas under pressure were as shown in Table 2.

TABLE 2

|  | 8 µL/min<br>first channel | 24 µL/min<br>second channel |
|---|---|---|
| cont | 393.8 | 438.2 |
| 50% dil | 195.8 | 110.2 |
| 50% dil + 0.5 U/ml vWF | 297.9 | 282.8 |
| 50% dil + 0.5 U/ml PCC | 343.8 | 21 |
| 1 U/ml heparin | 12 | 198 |
| 2 µg/ml abciximab | 258 | 6 |

According to the results of Examples 9 and 10, the formulation for supplementing blood coagulation factor (PCC) allowed remarkable recovery of thrombus formation in the first channel. Heparin, which is an anticoagulant, more strongly suppressed thrombus formation in the first channel, while abciximab, which is an antiplatelet drug, more strongly suppressed thrombus formation in the second channel. By applying higher tissue thromboplastin in the first channel, and allowing blood to flow at a higher flow rate in the second channel, contrast between the primary hemostatic capacity and the secondary hemostatic capacity could be more obvious.

Figure 10:
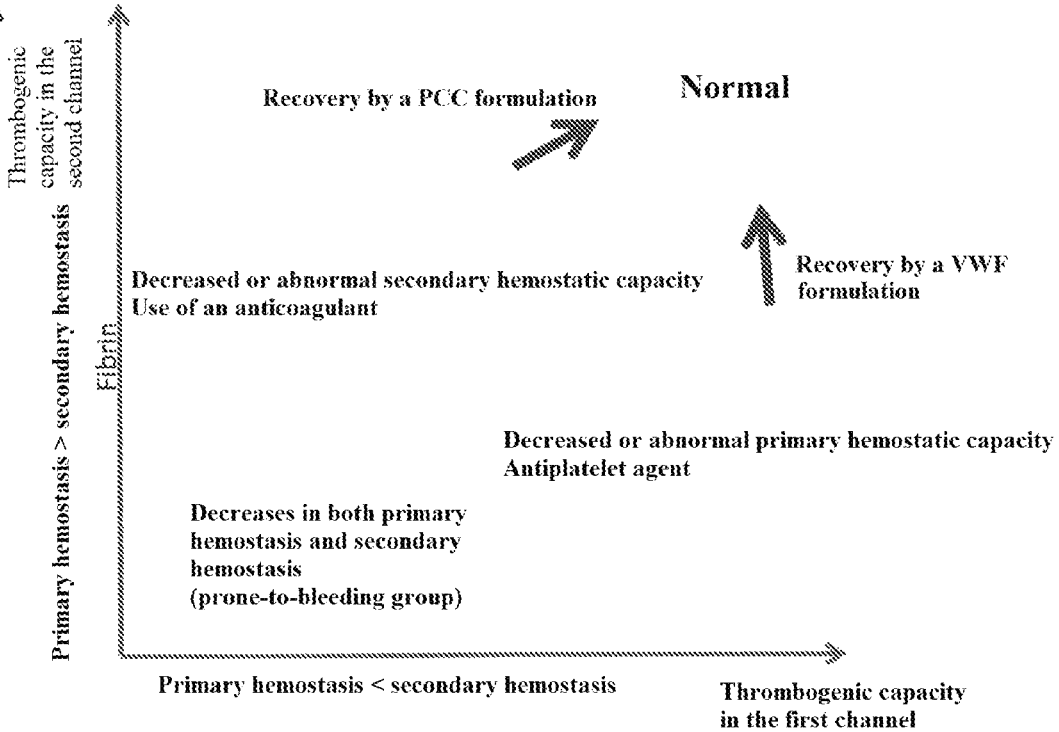
FIG. 10 is a schematic diagram illustrating the method for testing a blood property of the present invention.
Figure 10:
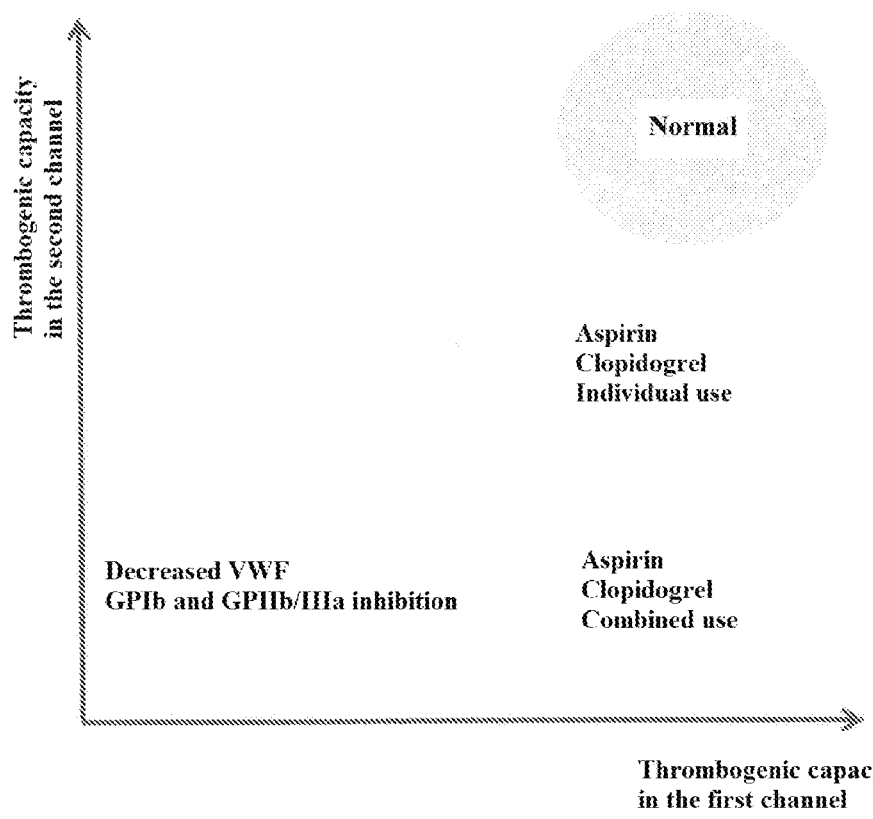

These results suggest the facts shown in FIG. 10 (A, B). Panel A shows cases where collagen and tissue thromboplastin are applied to both the first channel and the second channel. Panel B shows cases where collagen and tissue thromboplastin are applied only to the first channel, while only collagen is applied to the second channel.

INDUSTRIAL APPLICABILITY

Since the microchip of the present invention enables simultaneous analysis of two kinds of blood properties, that is, thrombus formation and platelet aggregation, using a small amount of blood, the microchip of the present invention is useful in the fields of medicine, diagnosis, tests, research, and the like.

DESCRIPTION OF SYMBOLS

A . . . Device for testing a blood property; 1 . . . microchip; 1a . . . first substrate; 1b . . . second substrate; 101, 111 . . . channel; 102, 112 . . . reaction section; 103, 113 . . . waste liquid storage section; 104, 114 . . . inlet; 105, 115 . . . air hole; 106, 116 . . . reservoir; 107, 117 . . . pump; 108, 118 . . . pressure sensor; 109, 119 . . . channel dividing wall.

The invention claimed is:

1. A microchip for testing a blood property, comprising a first channel and a second channel for allowing a blood sample(s) to flow inside, wherein
said first channel has a first reaction section coated with collagen and tissue thromboplastin, wherein the amount of tissue thromboplastin is no less than 1% by weight with respect to the collagen; and
said second channel has a second reaction section, wherein the second reaction section has been coated with collagen but not with tissue thromboplastin, wherein the blood sample has a higher flow rate in the second reaction section than in the first reaction section, wherein the first channel is adapted for measuring thrombus formation, and wherein the second reaction section is adapted for measuring platelet adhesion.

2. The microchip for testing a blood property according to claim 1, wherein each of said first reaction section and said second reaction section has a channel dividing wall along the direction of blood flow.

3. The microchip for testing a blood property according to claim 1, wherein each of said first reaction section and said second reaction section has a waste liquid storage section in its downstream side.

4. The microchip for testing a blood property according to claim 3, wherein said waste liquid storage section has an absorbent material containing an anticoagulant solution.

5. A device for testing a blood property, comprising: the microchip for testing a blood property according to claim 1; and a first blood storage container and a second blood storage container for introducing blood into said first channel and said second channel of said microchip for testing a blood property, wherein the first channel is adapted for measuring thrombus formation, and wherein the second reaction section is adapted for measuring platelet adhesion.

6. The device for testing a blood property according to claim 5, wherein said first blood storage container and said second blood storage container have been integrally molded.

7. The device for testing a blood property according to claim 5, further comprising: pumps connected to said first blood storage container and said second blood storage container, for allowing said blood sample(s) to flow from said first blood storage container and said second blood storage container into said first channel and said second channel; and pressure sensors for measuring the pressures applied to said pumps.

8. A method for simultaneously measuring platelet adhesion and thrombus formation to determine a blood property, said method comprising allowing a blood sample(s) to flow through said first and second channels using the device for testing a blood property according to claim 5, and measuring the thrombogenic capacity and the platelet function of blood.

9. A method for simultaneously measuring platelet adhesion and thrombus formation to determine a blood property using a device comprising a microchip which comprises a first channel and a second channel for allowing a blood sample(s) to flow inside, a first blood storage container and a second blood storage container for introducing blood into said first channel and said second channel of said microchip, wherein the first channel is adapted for measuring thrombus formation, and wherein the second reaction section is adapted for measuring platelet adhesion,
said method comprising allowing the blood sample(s) to flow through said first and second channels and measuring the thrombogenic capacity and the platelet function of blood, wherein, in said microchip, said first reaction section and said second reaction section have been coated with equivalent amounts of collagen and equivalent amounts of tissue thromboplastin, and the wall shear rate in said first reaction section is less than $1200 \text{ s}^{-1}$, and the wall shear rate in said second reaction section is not less than $1200 \text{ s}^{-1}$, wherein the wall shear rate in the second reaction section is not less than 1.5 times higher than the wall shear rate in the first reaction section.

10. The method for measuring a blood property according to claim 8, wherein said blood sample is a blood sample treated with a XII factor inhibitor(s), and with an anticoagulant(s) selected from the group consisting of plasma kallikrein inhibitors, low-molecular-weight heparin, heparan sulfate, and synthetic pentasaccharides.

* * * * *